United States Patent [19]

Phillipps et al.

[11] 4,352,798
[45] Oct. 5, 1982

[54] 11 α-AMINO-ANDROSTANES

[75] Inventors: Gordon H. Phillipps, Wembley; David C. Humber, Ealing; George B. Ewan, Northolt; Barry A. Coomber, Pinner, all of England

[73] Assignee: Glaxo Group Limited, London, England

[21] Appl. No.: 283,429

[22] Filed: Jul. 15, 1981

[30] Foreign Application Priority Data

Jul. 16, 1980 [GB] United Kingdom ............... 8023295
Mar. 2, 1981 [GB] United Kingdom ............... 8106488

[51] Int. Cl.³ .............................................. A61K 31/56
[52] U.S. Cl. .................................. 424/242; 260/397.1
[58] Field of Search ..................... 260/397.1; 424/242

[56] References Cited

U.S. PATENT DOCUMENTS

| | | | |
|---|---|---|---|
| 2,982,775 | 5/1961 | Oliveto et al. | 260/397.45 |
| 3,064,013 | 11/1962 | Babcock et al. | 260/397.3 |
| 3,215,713 | 11/1965 | Barton | 260/397.4 |
| 3,256,331 | 6/1966 | Jones et al. | 260/566 |
| 4,192,871 | 3/1980 | Phillipps et al. | 260/397.5 |
| 4,197,296 | 4/1980 | Phillipps et al. | 260/397.5 |

FOREIGN PATENT DOCUMENTS

| | | | |
|---|---|---|---|
| 853227 | 4/1977 | Belgium | 260/397.45 |
| 878069 | 9/1961 | United Kingdom | 260/397.45 |
| 887815 | 1/1962 | United Kingdom | 260/397.45 |
| 924421 | 4/1963 | United Kingdom | 260/397.45 |
| 1439605 | 6/1976 | United Kingdom | 260/397.45 |

OTHER PUBLICATIONS

Gratz and Rosenthal (Steroids, 1969, 14 (6) 739-753).
Pelah et al. (JACS. 1965, 87 (3), 574-580).
Marples (JCS Perkin I, 1974 (19), 2219-2225).
A. C. Campbell et al. (J C S Perkin I (1979), 1936-1940).
Hershbert et al. (Chem. and Ind. 1958, 1477-1478).
Rausser et al., J. Org. Chem., 1966, 31 (5) 1342-1346 and 1346-1349.

Primary Examiner—Elbert L. Roberts
Attorney, Agent, or Firm—Bacon & Thomas

[57] ABSTRACT

Compounds of formula

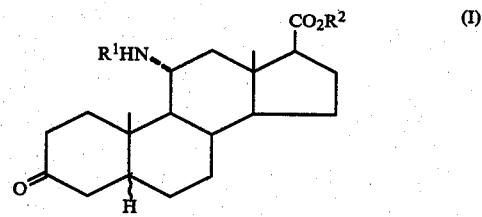

(wherein):
$R^1$ is a hydrogen atom, a $C_{1-8}$ alkyl group or a $C_{3-7}$ cycloalkyl group; and
$R^2$ is a hydrogen atom, a $C_{1-6}$ alkyl group or a $C_{3-6}$ cycloalkyl group; and the D-homo analogues thereof having the group $-CO_2R^2$ (wherein $R^2$ is as defined above) at the 17aβ-position and salts and zwitterionic forms thereof have activity as antidysrhythmic agents and may be applicable for treatment of ventricular dysrhythmias in humans or animals. The compounds may be provided in the form of compositions in admixture with pharmaceutical carriers and excipients and may be prepared by a variety of processes known for producing steroids of this type.

10 Claims, No Drawings

11 α-AMINO-ANDROSTANES

This invention relates to aminosteroids having antidysrhythmic activity, and in particular to certain compounds in the androstane series having a substituted or unsubstituted amino group at the 11α-position.

The aim of antidysrhythmic therapy is to return hazardous abnormal heart rhythms towards normal, or to reduce the likelihood of hazardous rhythms developing in patients at risk as a result of hypertension, atheromas, diabetes or heart conditions such as myocardial disease, ischaemia or infarction.

It is recognised that dysrhythmias in patients with heart attack and other conditions are treatable and preventable. There are several drugs available for the treatment of ventricular dysrhythmias but their application is limited by their lack of efficacy or by their toxicity which gives rise to various side effects.

Thus there is a demand for drugs suitable for use in the treatment of patients with dysrhythmias, and therefore in danger of sudden cardiac death. Furthermore, there is a demand for such drugs for administration, for example for long term prophylaxis, to patients at risk of developing dysrhythmias, in which case, activity on oral administration is desirable.

We have now discovered that a group of steroids having a primary or secondary amino group at the 11α-position and a 3-oxo group have promising antidysrhythmic activity.

Accordingly the invention provides 11α-amino-3-oxo-androstanes of the formula

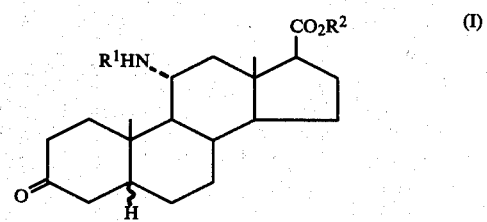

wherein $R^1$ is a hydrogen atom, a $C_{1-8}$ alkyl group or a $C_{3-7}$ cycloalkyl group; and $R^2$ is a hydrogen atom, a $C_{1-6}$ alkyl group or a $C_{3-6}$ cycloalkyl group, and the D-homo analogues thereof having the group —$CO_2R^2$ (wherein $R^2$ is defined above) at the 17aβ-position and salts and zwitterionic forms thereof.

The 5-hydrogen atom may be in the α- or β-configuration.

$R^1$ is preferably a $C_{1-8}$ alkyl group or a $C_{3-7}$ cycloalkyl group. $R^2$ is preferably a $C_{1-3}$ alkyl group.

Where $R^1$ is a cycloalkyl group, it may be, for example, a cyclobutyl, cyclopentyl, cyclohexyl or cycloheptyl group.

Where $R^1$ is an alkyl group it preferably has 3–7 carbon atoms, and may, for example, be a propyl, butyl, pentyl, isopentyl, hexyl, isohexyl or neohexyl group.

Where $R^2$ is a cycloalkyl group it may be, for example, a cyclopropyl, cyclobutyl, cyclopentyl or cyclohexyl group. Where $R^2$ is an alkyl group, it may be, for example, a methyl, ethyl, propyl, isopropyl, butyl or isopentyl group.

Where compounds having good activity following oral administration are desired, $R^2$ is preferably a methyl or ethyl group.

Ring D conveniently has 5 members.

Particularly preferred compounds are those in which $R^1$ is an isopentyl, hexyl, isohexyl, neohexyl, cyclopentyl or cyclohexyl group and $R^2$ is a methyl or ethyl group, especially a methyl group, and in which ring D has five members.

The compounds of formula (I) may form acid addition salts; physiologically acceptable salts are preferred. The compounds of formula (I) in which the group —$CO_2R^2$ represents a carboxyl group may also form salts with bases or exist as zwitterions.

Examples of acid addition salts are hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates. The hydrochlorides are preferred acid addition salts.

The salts with bases may be salts with inorganic bases such as alkali metal salts, e.g. sodium, potassium and lithium salts; alkaline earth metal salts, e.g. calcium and magnesium salts; and ammonium salts, or salts with organic bases for example amine salts.

Individual compounds which are preferred on the basis of their high antidysrhythmic activity include:
1. Methyl 11α-cyclohexylamino-3-oxo-5β-androstane-17β-carboxylate; and
2. Methyl 11α-cyclohexylamino-3-oxo-5α-androstane-17β-carboxylate and their physiologically acceptable acid addition salts, e.g. their hydrochlorides.

The compounds of the invention have been found to possess useful antidysrhythmic activity in the tests which have been carried out, and have potential as antidysrhythmic drugs.

The compounds may be used in the treatment of patients with disturbances of cardiac rhythm, whether arising spontaneously, or as a result of treatment with other drugs, e.g. cardiac glycosides, or as a consequence of myocardial ischaemia or infarction. Alternatively they may be used for the prophylactic treatment of patients at risk of cardiac rhythm disturbances or sudden coronary death.

The invention accordingly provides compounds of formula (I) and their physiologically acceptable acid addition salts for use in the therapy or prophylaxis of cardiac dysrhythmias in human beings or animals. The invention also provides compounds of formula (I) in association with instructions for their use in the therapy or prophylaxis of cardiac dysrhythmias in human beings or animals.

The compounds of the invention in which $R^1$ is a hydrogen atom may also be used as intermediates in the preparation of compounds of formula (I) in which $R^1$ is a $C_{1-8}$ alkyl or $C_{3-7}$ cycloalkyl group. Similarly the compounds of formula (I) in which $R^2$ is a hydrogen atom (or salts thereof) may also be used to prepare compounds in which $R^2$ is a $C_{1-6}$ alkyl or $C_{3-6}$ cycloalkyl group.

The compounds of the invention may additionally be used as intermediates in the preparation of the corresponding 3-hydroxy compounds, which also possess valuable antidysrhythmic activity.

The compounds of the invention may be formulated for administration in any convenient way, and the invention therefore includes within its scope pharmaceutical compositions comprising a compound of formula (I) or a physiologically acceptable salt thereof adapted for use in human or veterinary medicine. Such compositions may be presented for use in conventional manner with the aid of any necessary pharmaceutical carriers or excipients.

The compounds and their physiologically acceptable salts may for example be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, mucilage of starch or polyvinylpyrollidone; fillers, for example lactose, sugar, maize-starch, calcium phosphate or sorbitol; lubricants, for example magnesium stearate, talc, polyethylene glycol or silica; disintegrants, for example potato starch or sodium starch glycollate; or acceptable wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example sorbitol syrup, methyl cellulose, glucose-/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The compounds or their salts may also be formulated as suppositories, e.g. containing conventional suppository bases such as cocoa butter or other glycerides.

The compounds of the invention may also be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

When the compositions comprise dosage units, each unit will preferably contain at least 5 mg more preferably at least 10 mg of the active ingredient advantageously 25–500 mg. The daily dosage as employed for adult human treatment will preferably range from 25–2500 mg preferably 50–1000 mg depending on the route and frequency of administration. The compounds may be given in divided doses, for example 1–4 times per day.

The antidysrhythmic compounds according to the invention may be administered in combination with other therapeutic agents.

The compounds of the invention may be prepared by a number of different methods, using generally known techniques. Suitable methods are described below:

1. A substituent on the 11α-amino function may be introduced by reacting the corresponding compound in which $R^1$ is hydrogen with a compound of the formula $R^1X$ wherein $R^1$ is other than hydrogen and X is a readily displaceable atom or group such as halide (e.g. iodide), a hydrocarbylsulphonyloxy group (e.g. toluene-p-sulphonyloxy), a hydrocarbyloxysulphonyloxy group (e.g. methoxysulphonyloxy) or a dialkoxyphosphonyloxy group (e.g. dimethoxyphosphonyloxy). When carried out on compounds having a 17β-carboxyl group, such a reaction may result in esterification to form a compound in which $R^1 = R^2$. The group $R^2$ may, if not desired in the final product, subsequently be removed to yield the 17β-carboxylic acid, for example as set out under 7. below. The introduction of the substituent on the 11α-amino function is preferably carried out in the presence of a base (e.g. potassium carbonate or silver oxide) in solution at any suitable temperature from ambient to reflux (e.g. +20° to +80° C.). The reaction is conveniently effected in a suitable reaction solvent. Suitable solvents include ethers (e.g. dioxan), substituted amides (e.g. N,N-dimethylformamide or N,N-dimethylacetamide), sulphoxides (e.g. dimethylsulphoxide), alkanols (e.g. ethanol or methanol) or acetonitrile.

When X is a chlorine or bromine atom, the reaction may be facilitated by addition of an iodide such as sodium iodide.

The 11α-amino function may be introduced by reduction of the corresponding 11-oxime. Such a reduction may be effected with an alkali or alkaline earth metal in an alcohol and/or an amine and/or ammonia, e.g. sodium in n-propanol, if desired in the presence of a suitable solvent, e.g. tetrahydrofuran, at any suitable temperature up to and preferably at reflux.

The 11-oximes may themselves be prepared from the corresponding 11-oxo compounds. The 11-oxo compound may for example be reacted with hydroxylamine under strongly alkaline conditions in aqueous alcohol (e.g. ethanol), preferably at reflux. The reaction may also be carried out under acidic conditions (ca. pH 4), e.g. in buffered pyridine.

The severe conditions used in the reduction of the 11-oxime make it desirable that the 17β-alkoxycarbonyl substituent should be introduced after the formation of the 11α-amino group. Furthermore, the 3-oxo group should be introduced after the formation of the 11α-amino group.

2. A corresponding 11α-amino compound can be reductively "alkylated" with an appropriate monocarbonyl compound in the presence of a reducing agent, the term "alkylated" being used to refer to the introduction of a cycloalkyl group as well as an alkyl group. The reducing agents which may be used are those generally known for the reduction of imines, examples being formic acid (e.g. at any suitable temperature up to 100°–120° C., for example from room temperature up to 100°, and using the carbonyl compound as the reaction solvent, in the presence or absence of water), an alkali metal borohydride or cyanoborohydride (e.g. sodium borohydride or cyanoborohydride, using an alcohol such as ethanol as solvent, suitably at room temperature), iron pentacarbonyl or an alkali metal hydrogen iron carbonylate (e.g. $Fe(CO)_5$ or $MHFe(CO)_4$ where M is sodium or potassium, at any suitable temperature up to reflux using an ether such as tetrahydrofuran or an alcohol or aqueous alcohol as solvent), hydrogen in the presence of a metal catalyst (using an alcohol, e.g. ethanol, an ether, e.g. dioxan or an ester, e.g. ethyl acetate, as reaction solvent, conveniently at room temperature), or aluminium amalgam in the presence of water (conveniently at room temperature, and in the presence of an ether solvent such as tetrahydrofuran).

The metal catalyst may, for example, be a noble metal catalyst such as platinum, platinum oxide, palladium or rhodium. The catalyst may be supported, e.g. on charcoal or kieselguhr. A homogeneous catalyst such as tristriphenylphosphine rhodium chloride may also be used. If desired the intermediate imino compound may be isolated.

Thus, for example, the use of formaldehyde, acetaldehyde, 3-methylbutanal or cyclohexanone can provide the 11α-N-methyl, N-ethyl, N-iso-pentyl or N-cyclohexyl amines respectively. It will be appreciated that the conditions should be chosen to give predominantly the desired N-monosubstituted compound, and minimise production of the corresponding N,N-disubstituted compound. Reductive alkylation of the compounds of formula (I) in which $R^2$ is a hydrogen atom is preferably effected under basic conditions.

Under certain conditions employed in the above reactions, e.g. when a borohydride reducing agent is used, it may be necessary or desirable to protect the 3-oxo group as the corresponding ketal, e.g. as the 3,3-ethylenedioxy compound, which may be prepared by reacting the 3-oxo compound with ethylene glycol.

3. Conversion of a N,N-disubstituted 11α-amine into a N-mono-substituted or N-unsubstituted compound.

Compounds of the invention can be prepared from corresponding 11α-tertiary amino compounds by replacement of one or both of the groups by a hydrogen atom, e.g. by dealkylation using for example sodium nitrite followed by catalytic hydrogenolysis or de-aralkylation (e.g. de-benzylation) using for example catalytic hydrogenolysis. Thus, in particular, the compounds may be prepared by deprotection of a corresponding 11α-(protected amino) compound, for example an 11α-acylamino compound such as an 11α-trichloroethoxycarbonylamino, trifluoroacetylamino or formylamino compound or an 11α-silylamino compound e.g. an 11α-trimethylsilylamino compound. An acyl group may be removed by hydrolysis e.g. with acid or alkali. The trichloroethoxycarbonyl group may also be removed by reduction with, for example, zinc and acetic acid. Alternatively an arylmethyl protecting group such as a benzyl group may be removed by catalytic hydrogenation to produce the unprotected 11α-amino compound. A silyl group may be removed by e.g. solvolysis, with water (optionally containing acid or base) or an alcohol, or by treatment with an ionic fluoride such as tetrabutylammonium fluoride.

4. Esterification of a corresponding 17β-carboxylic acid.

Compounds of formula (I) in which $R^2$ is other than hydrogen may be prepared by reacting the corresponding 17β-carboxylic acid ($R^2$=hydrogen) or a reactive derivative thereof (e.g. an acid halide or anhydride or a salt) with the appropriate alcohol or alkyl or cycloalkyl halide. This reaction is preferably carried out at temperatures of $-20°$ C. to $+110°$ C., as is described for example in our British Patent Specification No. 1,380,246.

Where an alcohol is used in the esterification reaction, a coupling agent may be employed, for example a carbodiimide such as dicyclohexylcarbodiimide, preferably in the presence of a catalyst such as 4-dimethylaminopyridine.

Alternatively, esterification may be effected using a diazoalkane such as diazomethane.

The 17β-carboxylic acid starting material can conveniently be formed by oxidising the corresponding 17β-acetyl compound, i.e. a pregnan-20-one, using for example NaOBr in an aqueous inert solvent (e.g. dioxan).

When using certain of the above reagents, for example alkyl halides, it may be necessary to protect the 11α-amino group, for example as a trichloroethoxycarbonyl derivative.

5. Reduction of a corresponding $\Delta^{16}$-compound. The reduction may be effected by hydrogenation in the presence of a catalyst (e.g. a palladium catalyst) in a suitable solvent (e.g. an alcohol, ether or ester). The reaction may be effected conveniently at or about room temperature and atmospheric pressure in the presence of a tertiary base, e.g. triethylamine, and/or an acid, e.g. acetic acid.

The starting materials may be prepared by reaction of the corresponding 17-oxo-3-hydroxy compound with aqueous hydrogen cyanide to produce the 17-cyanohydrin which may be dehydrated to produce the $\Delta^{16}$-17β-cyano compound. This yields on hydrolysis the $\Delta^{16}$-17β-carboxylic acid and if required alkylation yields the corresponding $\Delta^{16}$-17β-carboxylic acid ester; oxidation of the 3-hydroxy group of the $\Delta^{16}$-17β-carboxylic acid or ester thereof gives the 3-oxo-$\Delta^{16}$ starting material.

6. Compounds of formula (I) in which $R^2$ is a hydrogen atom may be prepared from their corresponding esters, for example by hydrolysis under acidic or basic conditions. Examples of suitable acids for such hydrolysis include mineral acids such as hydrochloric acid; examples of suitable bases include alkali metal hydroxides and carbonates, such as sodium or potassium hydroxides or carbonates.

7. Compounds of formula (I) in which $R^2$ is other than hydrogen may also be prepared by transesterification i.e. by reaction of a corresponding compound having a 17β-ester group with an alcohol of formula $R^2OH$ in the presence of an acid or base catalyst at any temperature from room temperature to reflux, conveniently from 50° to 100° C., so as to produce a compound of formula (I) having a different 17β-ester group from the starting material; normally an excess of alcohol is used. Examples of suitable acid catalysts include mineral acids e.g. sulphuric and hydrochloric, and examples of suitable base catalysts include alkali metal hydroxides and carbonates, e.g. sodium or potassim hydroxides or carbonates.

8. The 3-oxo group may be introduced by oxidation of the corresponding 3α- or 3β-hydroxy compounds. A suitable oxidising agent is Jones reagent, which is prepared from chromium trioxide, concentrated sulphuric acid and water. The oxidation may be effected in a water-miscible solvent such as acetone and in the temperature range 5–40° C., preferably 20°–30° C.

9. Deketalisation.

As indicated above it is frequently necessary or desirable to protect the 3-oxo group during certain of the reaction stages, for example by ketalisation. The 3-oxo group may then be regenerated as a final step in the preparation. The ketal is preferably the 3,3-ethylenedioxy compound, in which case the 3-oxo group may be regenerated e.g. by hydrolysis in the presence of an acid, e.g. hydrochloric, sulphuric or acetic, or by an exchange reaction with a ketone, e.g. acetone in the presence of an acid catalyst, e.g. paratoluene sulphonic acid at a temperature from 0° to 100° C.

10. Salt formation.

Acid addition salts may be prepared by reaction of the free base with a suitable acid.

Base salts may be prepared by the reaction of the free acid with a suitable base. For example, alkali metal salts may be prepared by reaction with an alkali metal hydroxide, carbonate, bicarbonate or 2-ethylhexanoate.

The methods indicated above for preparing the compounds of the invention can be used as the last main step in a preparative sequence. The same general methods can be used for the introduction of the desired groups at an intermediate stage in the stepwise formation of the required compound, and it will be appreciated that these general methods can be combined in many different ways in such multi-stage processes. The sequence of the reactions in multi-stage processes should of course be chosen so that the reaction conditions used do not affect groups in the molecule which are desired in the final product.

The D-homo analogues of the compounds of the invention having a group —$CO_2R^2$ at the 17$\alpha\beta$-position may be prepared by essentially similar methods, using appropriate starting materials of the required structure.

The 3$\alpha$- and 3$\beta$-hydroxy steroids corresponding to the compounds of the invention, and which may be used at starting materials in certain of the processes set out above, may be prepared from 11-oxo-3$\alpha$-hydroxy-5$\alpha$-pregnan-20-one or its 3$\beta$-hydroxy isomer by oxidation to introduce a 17$\beta$-carboxyl group and introduction of the 11$\alpha$-amino group as described above.

The following examples illustrate the invention.

Melting points were determined in capillaries and are corrected. Optical rotations were determined at room temperature on 1% solutions in chloroform.

Preparative t.l.c. and column chromatography were carried out on silica.

Petrol refers to petroleum ether b.p. 60°–80° C.

Solutions were dried using anhydrous sodium sulphate.

IR spectra were determined in bromoform and refer to the carbonyl stretching frequency of the 17$\beta$-carboxylic acid ester group.

Jones reagent was prepared from chromium trioxide (26.8 g) and concentrated sulphuric acid (23.0 ml) diluted to 100 ml with water.

Preparation 1

11$\alpha$(2,2,2-trichloroethoxycarbonylamino)-3$\alpha$-(2,2,2-trichloroethoxycarbonyloxy)-5$\alpha$-pregnan-20-one A solution of 11$\alpha$-amino-3$\alpha$-hydroxy-5$\alpha$-pregnan-20-one (19.5 g) in dichloromethane (250 ml) and pyridine (26.5 ml) was cooled in an ice-bath during the addition of 2,2,2-trichloroethyl chloroformate (36 ml). On complete addition, water was carefully added and when no further reaction occurred the mixture was washed with 2M-HCl solution ($\times$2) and water. The solution was dried and evaporated to leave an oil (24.6 g) which was treated with ether to give the title compound (14.1 g) as a solid.

Preparation 2

3$\alpha$-Hydroxy-11$\alpha$-(2,2,2-trichloroethoxycarbonylamino)-5$\alpha$-androstane-17$\beta$-carboxylic acid Bromine (3.85 ml) was added dropwise to a solution of sodium hydroxide (11 g) in water (85 ml) keeping the temperature at $-10°$ C. Dioxan (42 ml) was added and the mixture was slowly added to a stirred solution of the product of Preparation 1 (15.5 g) in dioxan (280 ml) and water (85 ml) at 10° C. After complete addition the mixture was stirred for 2.5 h. $Na_2SO_3$ (4 g) was added and after 0.5 h the mixture was brought to pH 2 with 2M-HCl solution. Water (500 ml) was added and the mixture was extracted with chloroform ($\times$2). The extract was washed with water, dried and evaporated to leave a froth (9.5 g) which was purified by column chromatography eluted with EtOAc/petrol (1:1) to give the title compound (4.73 g). A portion was crystallised from ether/petrol, m.p. dec(gas evolved) 100° C., $[\alpha]_D + 19°$.

Preparation 3

Methyl 3$\alpha$-hydroxy-11$\alpha$-(2,2,2-trichloroethoxycarbonylamino)-5$\alpha$-androstane-17$\beta$-carboxylate A solution of the product of Preparation 2 (4 g) in DMF (80 ml) was stirred with $K_2CO_3$ (3.7 g) at 0° C. Methyl iodide (2.6 ml) was added and the mixture was stirred for 2 h. Water (300 ml) was added and the mixture was extracted with ether ($\times$3). The extract was washed with water, dried and evaporated to leave a froth which was purified by column chromatography eluted with EtOAc/petrol (1:2) and crystallised from ether to give the title compound (2.45 g), m.p. 167°–170° C., $[\alpha]_D + 25°$.

Preparation 4

11$\alpha$-(2,2,2-Trichloroethoxycarbonylamino)-3$\alpha$-[2,2,2-trichloroethoxycarbonyloxy]-5$\beta$-pregnan-20-one Pyridine (39 ml) and 2,2,2-trichloroethyl chloroformate (53 ml) were added to an ice-cooled solution of 11$\alpha$-amino-3$\alpha$-hydroxy-5$\beta$-pregnan-20-one (26.54 g) in dichloromethane (350 ml). After 2 h water (400 ml) was added and the organic phase was separated and evaporated to leave a brown oil which crystallised on trituration with ether/petrol to give the title compound (47.86 g), m.p. 174°–176° C., $[\alpha]_D + 60°$.

Preparation 5

3$\alpha$-Hydroxy-11$\alpha$-(2,2,2-trichloroethoxycarbonylamino)-5$\beta$-androstane-17$\beta$-carboxylic acid Bromine (12.5 ml) was added to a solution of sodium hydroxide (35.1 g) in water (270 ml) keeping the temperature between $-5°$ and 0° C. Dioxan (135 ml) was added and this mixture was added to a stirred solution of the product of Preparation 4 (47 g) in dioxan (900 ml) and water (270 ml) at 10° C. After 1 h sodium sulphite (12 g) was added and the mixture was diluted with water, brought to pH 2 with concentrated HCl solution and extracted with chloroform ($\times$2). The extract was washed with water ($\times$2), dried and evaporated to leave an oil which was taken up in dioxan. 2M-NaOH solution was added to give a pH $<$11 and the mixture was stirred for 3 h. The mixture was brought to pH 2 with concentrated HCl solution and diluted with water. The precipitate was extracted with chloroform ($\times$2) and the extract was washed with water, dried and evaporated to leave an oil which crystallised from ether/petrol to give the title compound (22.5 g), m.p 250°–251° C., $[\alpha]_D + 34°$.

Preparation 6

Methyl 3$\alpha$-hydroxy-11$\alpha$-(2,2,2-trichloroethoxycarbonylamino)-5$\beta$-androstane-17$\beta$-carboxylate Potassium carbonate (19.606 g) and methyl iodide (13.75 ml) were added to a stirred solution of the product of Preparation 5 (21.9 g) in dimethylformamide (400 ml) at 0° C. After 1.5 h the mixture was diluted with water (1.5 l) and extracted with ethyl acetate (×2). The extract was washed with brine (×2), dried and evaporated to leave the title compound (23.07 g) as a froth, $[\alpha]_D + 30°$.

Preparation 7

Methyl 11α-amino-3α-hydroxy-5α-androstane-17β-carboxylate

A solution of the product of Preparation 3 (2.4 g) in glacial acetic acid (25 ml) was stirred with zinc (2.5 g) for 4 hours. The zinc was removed by filtration and washed with water (50 ml) and ether (50 ml). The filtrate and washings were brought to pH 10 with 0.88 NH₃ solution and extracted with ester (×4). The extract was washed with water, dried and evaporated to leave a solid (1.65 g). A portion was crystallised from ether to give the title compound, m.p. 113°–116°, $[\alpha]_D + 38°$

Preparation 8

Methyl 11α-cyclopentylamino-3α-hydroxy-5α-androstane-17β-carboxylate

A solution of the product of Preparation 7 (2 g) in ethanol (20 ml) was treated with cyclopentanone (2 ml) and sodium cyanoborohydride (2 g) for 18 h. Incomplete reduction was found and sodium borohydride (0.05 g) was added. After 1 h the mixture was diluted with 5% NaHCO₃ solution (20 ml) and water (60 ml) and the precipitate was extracted with ether (×3). The extract was washed with water, dried and evaporated to leave an oil which was purified by column chromatography and preparative t.l.c. using chloroform:methanol (9:1) to give the title compound (1.47 g) as a froth, $[\alpha]_D + 12°$, $\nu_{max}$ 1724 cm⁻¹.

Preparation 9

Methyl 11α-amino-3α-hydroxy-5β-androstane-17β-carboxylate

Zinc powder (52.5 g) was added to a stirred solution of the product of Preparation 6 (22 g) in glacial acetic acid (600 ml). After 20 h the zinc was removed by filtration and washed with water. The filtrate and washings were evaporated to low bulk and then brought to pH 10 with 0.88 NH₃ solution. The oily precipitate was extracted with ethyl acetate (×2). The extract was washed with brine (×2), dried and evaporated to leave the title compound (13.56 g) as a froth $[\alpha]_D + 36°$.

Preparation 10

Methyl 3α-hydroxy-11α-(3-methylbutylamino)-5β-androstane-17β-carboxylate

Potassium carbonate (8.65 g) and 1-iodo-3-methylbutane (6.5 ml) were added to a stirred solution of the product of Preparation 9 (6 g) in dioxan (100 ml) and the mixture was heated at reflux for 50 h. Water (300 ml) was added to the cooled mixture and concentrated HCl solution was added to bring the pH to 2. The mixture was washed with ether and the ether wash was extracted with water (×4). The total aqueous phase was brought to pH 10 with 0.88 NH₃ solution and the precipitate was extracted with ether (×2). The extract was washed with brine (×2), dried and evaporated to leave a froth. A sample was purified by preparative t.l.c. using chloroform:methanol (9:1) to give the title compound (0.548 g), $[\alpha]_D + 8°$, $\nu_{max}$ 1726 cm⁻¹.

Preparation 11

Methyl 11α-cyclohexylamino-3α-hydroxy-5α-androstane-17β-carboxylate

Sodium cyanoborohydride (2 g) was added to a mixture of the product of Preparation 7 (2 g) and cyclohexanone (2.5 ml) in ethanol (30 ml). The mixture was kept at 21° C. for 5 h. 5% NaHCO₃ solution and water were added and the mixture was extracted with ether (×2). The extract was washed with water, dried and evaporated to leave a froth which was purified by column and preparative layer chromatography using CHCl₃:MeOH (9:1) to give the title compound (0.763 g) as a froth, $[\alpha]_D + 6°$, $\nu_{max}$ 1720 cm⁻¹.

Preparation 12

Methyl 3-oxo-11α-(2,2,2-trichloroethoxycarbonylamino)-5α-androstane-17β-carboxylate Jones reagent was added dropwise to a stirred solution of the product of Preparation 3 (0.3 g) in acetone (20 ml) until the reagent colour was not discharged. Water (150 ml) was added and the precipitate obtained was collected by filtration, washed with water, dried and crystallised from ethyl acetate/petrol to give the title compound (0.19 g), m.p. 208°–209° C., $[\alpha]_D + 41°$.

Preparation 13

Methyl 3β-hydroxy-11α-(2,2,2-trichloroethoxycarbonylamino)-5α-androstane-17β-carboxylate Sodium borohydride (1 g) was added to a solution of the product of Preparation 12 (12 g) in methanol (200 ml). After 15 min. the mixture was slowly diluted with water to 1.5 l. The solid (11.2 g) was collected by filtration, washed with water, dried and crystallised from aqueous methanol to give the title compound (8.12 g), m.p. 140°–143° C., $[\alpha]_D + 8°$.

Preparation 14

Methyl 11α-amino-3β-hydroxy-5α-androstane-17β-carboxylate

Zinc (10 g) was added to a stirred solution of the product of Preparation 13 (10.5 g) in glacial acetic acid (50 ml) for 4 h. The zinc was removed by filtration and washed with water (10 ml). The filtrate and washings were brought to pH 11 with 50% NaOH solution and extracted with ether (×3). The extract was washed with water, dried and evaporated to leave a froth (5.81 g). A portion was purified by preparative t.l.c. using 2% NH₃ solution in methanol to give the title compound (0.382 g), $[\alpha]_D + \div °$, $\nu_{max}$ 1720 cm⁻¹.

Preparation 15

Methyl 3β-hydroxy-11α-3-(methylbutylamino)-5α-androstane-17β-carboxylate

The product of Preparation 14 (5.2 g) was dissolved in ethanol (100 ml) and the solution was stirred and heated at reflux with 1-bromo-3-methyl-butane (10 ml), potassium carbonate (7 g) and sodium iodide (0.2 g) for 72 h. Water (200 ml) was added and the mixture was extracted with ether (×3). The extract was washed with water, dried and evaporated to leave an oil which was purified by column chromatography on silica (200 g) eluted with CHCl$_3$:MeOH (19:1) to give an oil. A portion was further purified by preparative t.l.c. using ether to give an oil.

The oil (0.62 g) was dissolved in methanol (30 ml) and the solution was heated at reflux with concentrated H$_2$SO$_4$ (2.5 ml) for 18 h. The cooled mixture was brought to pH 11 with 50% NaOH solution and diluted with water (100 ml). The precipitate was extracted into ether ($\times$3). The extract was washed with water, dried and evaporated to give the title compound (0.6 g), $[\alpha]_D + 10°$, $\nu_{max}$ 1720 cm$^{-1}$.

Preparation 16

Methyl 11α-cyclohexylamino-3α-hydroxy-5β-androstane-17β-carboxylate

Cyclohexanone (2.9 ml) and sodium cyanoborohydride (2.512 g) were added to a stirred solution of methyl 11α-amino-3α-hydroxy-5β-androstane-17β-carboxylate (2.505 g) in ethanol (30 ml). After 5 h the mixture was diluted with 5% NaHCO$_3$ solution and extracted with ether ($\times$2). The extract was washed with water ($\times$2), dried Na$_2$SO$_4$) and evaporated to leave a froth (2.544 g). A sample (0.39 g) was purified by preparative t.l.c. using CHCl$_3$:MeOH (19:1) to give the title compound $[\alpha]_D - 9°$, $\nu_{max}$ 1725 cm$^{-1}$.

EXAMPLE 1

Methyl 11α-(3-methylbutylamino)-3-oxo-5β-androstane-17β-carboxylate

Jones reagent (8 ml) was added dropwise to a stirred solution of the product of Preparation 10 (4 g) in acetone (300 ml). After 2 h the mixture was diluted with water (500 ml) and brought to pH 10 with 0.88 NH$_3$ solution. The mixture was extracted with ether and filtered before separation of the organic phase. The aqueous phase was further extracted with ether and the total extract was washed with water ($\times$2), dried and evaporated to leave the title compound (3.198 g) as an oil $[\alpha]_D + 3°$.

EXAMPLE 2

Methyl 11α-cyclopentylamino-3-oxo-5α-androstane-17β-carboxylate

Jones reagent was added dropwise to a stirred solution of the product of Preparation 8 (1.4 g) in acetone (120 ml) until the reagent colour was not discharged. The mixture was brought to pH 10 with 0.88 NH$_3$ solution and diluted with water (300 ml). The precipitate was extracted with ether ($\times$3) and the extract was washed with water, dried and evaporated to leave a solid (1.4 g). A portion (0.2 g) was crystallised from ether to give the title compound, m.p. 156°–158° C., $[\alpha]_D - 3°$.

EXAMPLE 3

Methyl 11α-cyclohexylamino-3-oxo-5β-androstane-17β-carboxylate

Jones reagent (4.25 ml) was added dropwise to a stirred solution of the product of Preparation 16 (2.164 g) in acetone (150 ml) until the reagent colour was not discharged. After 2.5 h the mixture was diluted with water (300 ml) and brought to pH 10 with 0.88 NH$_3$ solution. The mixture was shaken with ether (250 ml) and the total liquid was filtered. The aqueous phase was separated and extracted with ether (250 ml). The combined organic phase was washed with water ($\times$2), dried and evaporated to leave an oil (1.119 g). A portion (0.32 g) was purified by preparative t.l.c. using CHCl$_3$:MeOH (19:1) to give the title compound $[\alpha]_D - 9°$ (CHCl$_3$c=1.0%), $\nu_{max}$ 1710 cm$^{-1}$, 1725 cm$^{-1}$ (CHBr$_3$).

EXAMPLE 4

Methyl 11α-cyclohexylamino-3-oxo-5α-androstane-17β-carboxylate

Jones reagent was added dropwise to a stirred solution of the product of Preparation 11 (3.095 g) in acetone (225 ml) until the reagent colour was not discharged. After 2.5 h the mixture was diluted with water (300 ml) and brought to pH 10 with 0.88 NH$_3$ solution. The mixture was shaken with ether (250 ml) and the total liquid was filtered. The aqueous phase was separated and extracted with ether (250 ml) and the combined organic phase was washed with water ($\times$2), dried and evaporated to leave an oil (2.099 g). A sample (0.5 g) was purified by preparative t.l.c. using CHCl$_3$:MeOH (19:1) and crystallised from petrol to give the total compound m.p. 91°–93° C., $[\alpha]_D - 14°$.

EXAMPLE 5

Methyl 11α-(3-methylbutylamino)-3-oxo-5α-androstane-17β-carboxylate

Jones reagent was added dropwise to a solution of the product of Preparation 15 (1.2 g) in acetone (150 ml) until the reagent colour was not discharged. The mixture was brought to pH 10 with 0.88 NH$_3$ solution, diluted with water (300 ml) and extracted with ether ($\times$3). The extract was washed with water, dried and evaporated to leave a froth. The froth was dissolved in methanol (120 ml) and the solution was heated at reflux with conc. H$_2$SO$_4$ (4 ml) for 5 h. The cooled mixture was brought to pH 10 with 0.88 NH$_3$ solution, diluted with water and extracted with ether ($\times$3). The extract was washed with water, dried and evaporated to leave a froth. Purification by preparative t.l.c. in CHCl$_3$:MeOH (9:1) produced a froth (0.492 g) which was crystallised from petrol to give the title compound, m.p. 86°–89° C., $[\alpha]_D + 15°$.

EXAMPLE 6

Methyl 11α-cyclohexylamino-3-oxo-5β-androstane-17β-carboxylate hydrochloride 0.0979 M hydrochloric acid (2.38 ml) was added to a suspension of the product of Example 3 in water (5 ml) and the mixture stirred until a clear solution was obtained. The mixture was made up to 10 ml with water to give a 1% solution of the hydrochloride salt having a pH of 3.1.

EXAMPLE 7

Methyl 11α-cyclohexylamino-3-oxo-5α-androstane-17β-carboxylate hydrochloride 0.0979 M hydrochloric acid (2.38 ml) was added to a suspension of the product of Example 4 in water (5 ml) and the mixture stirred until a clear solution was obtained. The mixture was made up to 10 ml with water to give a 1% solution of the hydrochloride salt having a pH of 2.7.

EXAMPLE A

| Tablet | mg/tablet |
|---|---|
| Methyl 11α-cyclohexylamino-3-oxo-5α-androstane-17β-carboxylate hydrochloride | 108.00 |
| Maize starch | 138.00 |
| Polyvinyl pyrrolidone | 2.5 |
| Sodium starch glycolate | 7.5 |
| Magnesium stearate | 2.0 |
| Tablet weight | 258.0 |

Sieve the steroid and maize starch through a 40 mesh screen. Blend the maize starch with the steroid in a suitable blender. Make a 5–10% w/v aqueous solution of the polyvinyl pyrrolidone. Add this solution to the mixing powder and mix until granulated. Pass the granulate through a number 12 screen. Dry the granules at 50° C. in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine.

EXAMPLE B

Intravenous Injection

| Methyl 11α-cyclohexylamino-3-oxo-5α-androstane-17β-carboxylate hydrochloride equivalent to 1 to 10mg of free base | |
|---|---|
| Sodium chloride | sufficient for isotonicity |
| water for injections | to 1 ml |

Dissolve the steroid and the sodium chloride in some of the water. If necessary adjust the pH with sodium hydroxide solution or hydrochloric acid solution. Make up to volume with water and stir until homogeneous. Filter the solution into clean glass vials and seal by fusion. The solution may be sterilised by autoclaving or filtration or preparing under aseptic conditions.

We claim:
1. Compounds of formula

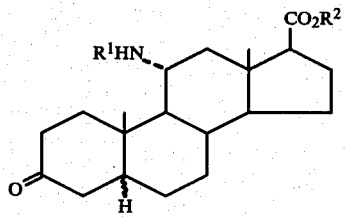

(wherein:
$R^1$ is a hydrogen atom, a $C_{1-8}$ alkyl group or a $C_{3-7}$ cycloalkyl group; and
$R^2$ is a hydrogen atom, a $C_{1-6}$ alkyl group or a $C_{3-6}$ cycloalkyl group; and the D-homo analogues thereof having the group $-CO_2R^2$ (wherein $R^2$ is as defined above) at the 17aβ-position and salts and zwitterionic forms thereof.

2. Compounds as claimed in claim 1 wherein $R^1$ is an isopentyl, hexyl, isohexyl, neohexyl, cyclopentyl or cyclohexyl group and $R^2$ is a methyl or ethyl group, wherein ring D has 5 members.

3. Compounds as claimed in either of claims 1 and 2 in the form of physiologically acceptable acid addition salts.

4. Compounds as claimed in claim 3 in the form of hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates.

5. A compound as claimed in claim 1 which is methyl 11α-cyclohexylamino-3-oxo-5β-androstane-17β-carboxylate and its physiologically acceptable acid addition salts.

6. A compound as claimed in claim 1 which is methyl 11α-cyclohexylamino-3-oxo-5α-androstane-17β-carboxylate and its physiologically acceptable acid addition salts.

7. Compounds as claimed in either of claims 5 and 6 in the form of their hydrochlorides.

8. Pharmaceutical compositions comprising at least one compound of formula (I) as claimed in claim 1 or a physiologically acceptable acid addition salt thereof in admixture with one or more pharmaceutical carriers or excipients.

9. A process for the manufacture of a compound of formula (I) as claimed in claim 1 which comprises
(A) (where a compound in which $R^1$ is other than hydrogen is desired) reacting a corresponding 11α-amino compound or a corresponding 11α-amino-17β-carboxylic acid with a compound of formula $R^1X$ wherein $R^1$ is as defined in claim 1 (other than hydrogen) and X is a readily displaceable atom or group;
(B) (where a compound in which $R^1$ is other than hydrogen is desired) reacting a corresponding 11α-amino compound in the presence of a reducing agent with a monocarbonyl compound serving to introduce the group $R^1$ as defined in claim 1, other than hydrogen;
(C) converting a corresponding N,N-disubstituted 11α-amino into an N-monosubstituted or N-unsubstituted compound;
(D) (where a compound in which $R^2$ is other than hydrogen is desired) esterifying a corresponding 17β-carboxylic acid;
(E) reducing a corresponding $\Delta^{16}$ compound with a suitable reducing agent;
(F) (where a compound in which $R^2$ is hydrogen is desired) hydrolysing a corresponding compound in which $R^2$ is other than hydrogen;
(G) (where a compound in which $R^2$ is other than hydrogen is desired) transesterifying a corresponding compound having a 17β-ester group other than the desired group $R^2$ with an alcohol of formula $R^2OH$, wherein $R^2$ is as defined in claim 1, other than hydrogen;
(H) oxidising a corresponding 3α or 3β-hydroxy compound; or
(I) deprotecting a corresponding compound having a protected 3-oxo group followed, where necessary, by the formation of acid addition or base salts.

10. A method of treatment or prophylaxis of a human or animal subject suffering from or liable to ventricular dysrhythmias which comprises administering to said subject an effective amount of one or more compounds as claimed in claim 1.

* * * * *